(12) United States Patent
Rothman et al.

(10) Patent No.: US 6,331,299 B1
(45) Date of Patent: Dec. 18, 2001

(54) METHOD FOR TREATMENT OF CANCER AND INFECTIOUS DISEASE AND COMPOSITIONS USEFUL IN SAME

(75) Inventors: James E. Rothman, New York, NY (US); F. Ulrich Hartl, Munich (DE); Mee H. Hoe, New York, NY (US); Alan Houghton, New York, NY (US); Yoshizumi Takeuchi, Kobe (JP); Mark Mayhew, Tarrytown, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/011,648

(22) PCT Filed: Aug. 16, 1996

(86) PCT No.: PCT/US96/13233

§ 371 Date: Feb. 13, 1998

§ 102(e) Date: Feb. 13, 1998

(87) PCT Pub. No.: WO97/06685

PCT Pub. Date: Feb. 27, 1997

Related U.S. Application Data (60) Provisional application No. 60/002,479, filed on Aug. 18, 1995, and provisional application No. 60/002,490, filed on Aug. 18, 1995.

(51) Int. Cl.[7] ................................................. A61K 48/00

(52) U.S. Cl. ................. 424/93.21; 435/69.1; 435/320.1; 435/325; 435/455; 424/450

(58) Field of Search .................. 424/93.21; 435/455, 435/69.1, 320.1, 325

(56) References Cited

U.S. PATENT DOCUMENTS

| | | | |
|---|---|---|---|
| 5,348,945 | 9/1994 | Berberian et al. | 514/21 |
| 5,750,119 | 5/1998 | Srivastava et al. | 514/2 |
| 5,962,262 | * 10/1999 | Hillman et al. | 435/69.1 |

FOREIGN PATENT DOCUMENTS

| | | |
|---|---|---|
| 9317712 | 9/1993 | (WO) . |
| 9411513 | 5/1994 | (WO) . |
| 9429459 | 12/1994 | (WO) . |
| 9524923 | 9/1995 | (WO) . |
| 9610411 | 4/1996 | (WO) . |
| 9706281 | 2/1997 | (WO) . |
| 9706685 | 2/1997 | (WO) . |
| 9710000 | 3/1997 | (WO) . |
| 9710001 | 3/1997 | (WO) . |
| 9710002 | 3/1997 | (WO) . |
| 9726910 | 7/1997 | (WO) . |
| 9942121 | 7/1999 | (WO) . |

OTHER PUBLICATIONS

Mastrangelo et al. (Seminars in Oncology, vol. 23, 1, pp. 4–21, 1996.*
Luckacs et al., (Cancer Gene Therapy, vol. 1, 3, p. 217), 1994.*
Riddell et al. (Nature Medicine, vol. 2, 2:216–223, 1996).*
Ngo et al., Computational Complexity Protein Structure Prediction and the Levinthal Paradox, 1994, Birkhauser Boston, vol. 14 pp. 492–495.*
U.S. application No. 60/075,358, Podack et al., filed Mar. 30, 1999.
Huang, et al., 2000, In Vivo Cytotoxic T Lymphocytes Elicitation by Mycobacterial Heat Shock Protein 70 Fusion Proteins Maps a Discrete Domain and Is CD4+ T Cell Independent, J.. Exp. Med., 191:403–408.
Todryk et al., 1999, Heat Shock Protein 70 Induced During Tumor Cell Killing Induces Th1 Cytokines and Targets Immature Dendritic Cell Precursors to Enhance Antigen Uptake, J. Immumnology, 163:1398–1408.
Yamazaki et al., 1999, Cutting Edge:Tumor Secreted Heat Shock–Fusion Protein Elicits CD8 Cells for Rejection, J. Immunology 163:5178–5182.
Melcher et al., 1998, Tumor Immunogenicity is Determined by the Mechanism of Cell Death Via Induction of Heat Shock Protein Expression, Nature Medicine 4:581–587.
Wells, et al., 1998, Hsp72–mediated Augmentation of MHC Class 1 Surface Expression and Endogenous Antigen Presentation, In Immunol 10:609–617.7.
Flajnik et al., 1991, Which Came First, MHC Class I or Class II?, Immunogenetics, 33:295–300.
Auger, et al., 1996, Nature Medicine 2:306–310.
Giboa, 1996, Seminars in Oncology 23:101–107.
Minami et al., 1996, J. Biol, Chem. 271:19617–19624.
Nieland, et al., 1996, Proc. Natl. Acad. Sci. USA 93:6135–6139.
Zhu, et al., 1996, Science 272:1606–1614.
Bauer, et al., 1995, Scand. J. Immunol. 42:317–323.

(List continued on next page.)

*Primary Examiner*—Dave T. Nguyen
(74) *Attorney, Agent, or Firm*—Baker Botts; Lisa B. Kole; Alicia A. Russo (57) ABSTRACT

Administration of expressible polynucleotides encoding eukaryotic heat shock proteins to mammalian cells leads to the stimulation of an immune response to antigens present in those cells. This makes it possible to stimulate an immune response to target antigens, including target tumor antigens or antigens associated with an infectious disease, without having to isolate a unique antigen or antigen-associated with an infectious disease, without having to isolate a unique antigen or antigen-associated heat shock protein for each target antigen by administering to a mammalian subject or to a group of mammalian cells containing the antigen, an expressible polynucleotide encoding a heat shock protein. The expressed heat shock protein may have the same structure as native heat shock proteins, or may have a modified form adapted to control the trafficking of the expressed heat shock protein within the cells.

6 Claims, 5 Drawing Sheets

OTHER PUBLICATIONS

Blachere and Srivastava, 1995, Seminars in Cancer Biology 6:349–355.
Edginton, 1995, Bio/Technol. 13:1442–1444.
Greene et al., 1995, J. Biol. Chem. 270:2967–2978.
Hohfeld et al., 1995, Cell 83:589–598.
Lowrie et al., 1995, J. Cell. Biochem. Suppl. 0(19b):220.
McCarty et al., 1995, J. Mol. Biol. 249:126–137.
Multhoff, et al., 1995, Int. J. Cancer 61:272–279.
Zhu, et al., 1995, Scand. J. Immunol. 42:557–563.
Barrios et al., 1994, Clin. Exp. Immunol. 98:224–228.
Barrios et al., 1994, Clin. Exp. Immunol. 98:229–233.
Del Guidice, 1994, Experientia 50:1061–1066.
Lowrie et al., 1994, Vaccine 12:1537–1540.
Nygren, et al., 1994, Trends Biotechnol. 12(5):184–188.
Retzlaff et al., 1994, Infect. Immun. 62:5689–5693.
Schmid et al., 1994, Science 263:971–973.
Sato et al., 1994, Proc. Annu. Meet. Am. Assoc. Cancer Res. 35:A2959.††.
Silva and Lowrie, 1994, Immunology 82:244–248.
Srivastava, 1994, Experentia 50:1054–1060.
Srivastava and Udono, 1994, Current Opinion in Immunology 6:728–732.
Blond–Elguindi et al., 1993, Cell 75:717–728.
DeNagel and Pierce, et al., 1993, Critical Reviews in Immunology 13:71–81.
Mustafa, et al., 1993, Infection and Immunity 61:5294–5301.
Palleros et al., 1993, Nature 365:664–666.
Perraut, 1993, Clin Exp. Immunol. 93:382–386.
Srivastava, 1993, Adv. Cancer Res. 62:153–177.
Yamamoto, et al., 1993 Infection and Immunity 61:2154–2161.
Barrios, et al., 1992, Euro. J. Immunol. 22:1365–1372.
Davidoff, et al., 1992, Proc. Nat'l. Acad. Sci. USA, 89:3439–3442.
Pidoux et al., 1992, EMBO J. 11:1583–1591.
Lussow, et al., 1991, J. Eur. Immmunolo. 21:2297–2302.
Srivastava and Maki, 1991, Current Topics in Micorobiology and Immunology, 167:109–121.
Flynn et al., 1989, Science 245:385–390.
Pelham, 1988, EMBO J. 7:913–918.
Munro and Pelham, 1987, Cell, 480:899–907.
Srivastava, et al., 1986, Proc. Natl. Acad. Sci. USA, 83:3407–3411.
Ullrich, et al., Proc. 1986, Proc. Natl. Acad. Sci. U.S.A., 83:3121–3125.
Von Heijne, 1985, J. Mol. Biol. 184:99–105.

* cited by examiner

FIG.2F ically reduced.

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 27
       (B) TYPE: nucleic acid
       (C) STRANDEDNESS: double
       (D) TOPOLOGY: linear (ii) MOLECULE TYPE: Genomic DNA (iii) HYPOTHETICAL:no (iv) ANTI-SENSE: yes (v) FRAGMENT TYPE: internal (vi) ORIGINAL SOURCE:
       (A) ORGANISM: mouse (ix) FEATURE:
       (D) OTHER INFORMATION: amplification primer for gp96

(xi) SEQUENCE DESCRIPTION: SEQ ID NO:1:

GCGGATCCTA GTTTAGACCA GTATGTC                27

(2) INFORMATION FOR SEQ ID NO: 2:

(i) SEQUENCE CHARACTERISTICS:
       (A) LENGTH: 44
       (B) TYPE: nucleic acid
       (C) STRANDEDNESS: double
       (D) TOPOLOGY: linear (ii) MOLECULE TYPE: Genomic DNA (iii) HYPOTHETICAL:no (iv) ANTI-SENSE: no (v) FRAGMENT TYPE: internal (vi) ORIGINAL SOURCE:
       (A) ORGANISM: mouse (ix) FEATURE:
       (D) OTHER INFORMATION: amplification primer for gp96

(xi) SEQUENCE DESCRIPTION: SEQ ID NO:2:

CCGAATTCGG GCCCCAATTT ACTCTGTAGA TTCCTTTTCT GTTT     44

METHOD FOR TREATMENT OF CANCER AND INFECTIOUS DISEASE AND COMPOSITIONS USEFUL IN SAME The present application is based on International Application No. PCT/US96/13223, filed Aug. 16, 1996, which is based on provisional U.S. Application Nos. 60/002/479 and 60/002/490, both filed on Aug. 18, 1995.

The invention described herein was made in the course of work under NIH Core Grant No. CA 08748. The United States government may have certain rights in this invention.

BACKGROUND OF THE INVENTION

This application relates to the use of heat shock proteins and similar peptide-binding proteins to stimulate an immunological response against antigens, including cancer-related antigens, autoimmune antigens and infectious disease antigens, found in a mammalian host.

Heat shock proteins were originally observed to be expressed in increased amounts in mammalian cells which were exposed to sudden elevations of temperature, while the expression of most cellular proteins is significantly reduced. It has since been determined that such proteins are produced in response to various types of stress, including glucose deprivation. As used herein, the term "heat shock protein" will be used to encompass both proteins that are expressly labeled as such as well as other stress proteins, including homologs of such proteins that are expressed constitutively (i.e., in the absence of stressful conditions). Examples of heat shock proteins include BiP (also referred to as grp78), hsp/hsc70, gp96 (grp94), hsp60, hsp40 and hsp90.

Heat shock proteins have the ability to bind other proteins in their non-native states, and in particular to bind nascent proteins emerging from the ribosomes or extruded into endoplasmic reticulum. Hendrick and Hartl, *Ann. Rev. Biochem.* 62: 349–384 (1993); Hartl, *Nature* 381: 571–580 (1996). Further, heat shock proteins have been shown to play an important role in the proper folding and assembly of proteins in the cytosol, endoplasmic reticulum and mitochondria; in view of this function, they are referred to as "molecular chaperones". Frydman et al., *Nature* 370: 111–117 (1994); Hendrick and Hartl., *Ann. Rev. Biochem.* 62:349–384 (1993); Hartl., *Nature* 381:571–580 (1996).

For example, the protein BiP, a member of a class of heat shock proteins referred to as the hsp70 family, has been found to bind to newly synthesized, unfolded $\mu$ immunoglobulin heavy chain prior to its assembly with light chain in the endoplasmic reticulum. Hendershot et al.,*J. Cell Biol.* 104:761–767 (1987). Another heat shock protein, gp96, is a member of the hsp90 family of stress proteins which localize in the endoplasmic reticulum. Li and Srivastava, *EMBO J.* 12:3143–3151 (1993); Mazzarella and Green,*J. Biol. Chem.* 262:8875–8883 (1987). It has been proposed that gp96 may assist in the assembly of multi-subunit proteins in the endoplasmic reticulum. Wiech et al., *Nature* 358:169–170 (1992).

It has been observed that heat shock proteins prepared from tumors in experimental animals were able to induce immune responses in a tumor-specific manner; that is to say, heat shock protein purified from a particular tumor could induce an immune response in an experimental animal which would inhibit the growth of the same tumor, but not other tumors. Srivastava and Maki, 1991, *Curr. Topics Microbiol.* 167: 109–123 (1991). The source of the tumor-specific immunogenicity has not been confirmed. Genes encoding heat shock proteins have not been found to exhibit tumor-specific DNA polymorphism. Srivastava and Udono, *Curr. Opin. Immunol.* 6:728–732 (1994). High resolution gel electrophoresis has indicated that gp96 may be heterogeneous at the molecular level. Feldweg and Srivastava,*Int. J. Cancer* 63:310–314 (1995). Evidence suggests that the source of heterogeneity may be populations of small peptides adherent to the heat shock protein, which may number in the hundreds. Id. It has been proposed that a wide diversity of peptides adherent to tumor-synthesized heat shock proteins may render such proteins capable of eliciting an immune response in subjects having diverse HLA phenotypes, in contrast to more traditional immunogens which may be somewhat HLA-restricted in their efficacy. Id.

Lukacs et al., *J. Exp. Med.* 178: 343–348 (1993), have reported the transfection of tumor cells with a mycobacterial heat shock protein-encoding gene, and the observation that the transfected cells lose tumorigenicity and induce what appears to be T-cell mediated protection against tumors in mice immunized using the transfected cells. Lukacs et al. suggest that the loss of tumorigenicity could result from the interaction of the heat shock protein with p53 via increased efficiency of chaperone activity to produce proper folding and conformation of otherwise ineffective p53 protein. They further suggest that the highly immunogenic nature of the 65 kD bacterial hsp enhances the recognition of other, tumor-associated antigen molecules.

It has been suggested in the literature that mycobacterial heat shock proteins may play a role in the onset of autoimmune diseases such a rheumatoid arthritis. Thus, the practical utility of such bacterial proteins in vaccines for the treatment of humans is questionable. It is an object of the present invention to provide vaccine compositions which can be used to stimulate an immune response to antigens, including tumor and infectious disease antigens, present in mammalian cells without the introduction of mycobacterial proteins.

SUMMARY OF THE INVENTION

It has now been found that administration of expressible polynucleotides encoding eukaryotic heat shock proteins to mammalian cells leads to the stimulation of an immune response to antigens present in those cells. This makes it possible to stimulate an immune response to treat a subject's disease condition, including an immune response to a tumor or an infectious disease, without having to isolate or characterize an antigen associated with the disease. Thus, the present invention provides a method for stimulating a therapeutic or prophylactic immune response in a mammalian subject by treating the subject or a group of cells from the subject with an expressible polynucleotide encoding a eukaryotic heat shock protein. The expressed heat shock protein may have the same structure as native heat shock proteins, or may be a modified form adapted to control the trafficking of the expressed heat shock protein within the cells.

DETAILED DESCRIPTION OF THE INVENTION

The present invention provides a method for inducing or enhancing an immune response to an antigen present in a target group of cells without requiring prior identification, characterization or isolation of the antigen. The method of the invention may be used to induce an immune response to the antigen in the case where there is no existing detectable disease-related immune response prior to practicing the method, or to enhance the disease-related immune response to a greater level. For purposes of simplicity, the specification and claims of this application will use the term "stimulating an immune response" to encompass both inducing a new immune response and enhancing a pre-existing immune response.

We have found that administration of expressible polynucleotides encoding eukaryotic heat shock proteins to mammalian cells leads to the stimulation of an immune response to antigens present in those cells. While we do not intend to be bound by any particular mechanism, the full potential of our observations is beat understood in the context of two mechanistic models which explain the observations.

The first mechanism is based on the fact that heat shock proteins like BiP and gp96 are normally localized in the endoplasmic reticulum and are known to bind peptides and proteins in this location, and the belief that such binding may be a step in the presentation of an antigen to the immune system. Increasing the concentration of one or more heat shock proteins resident in the endoplasmic reticulum may cause an improvement in the efficiency of this process, and thus an increased immune response to the antigens present in the transfected cells.

The second mechanism is based upon the understanding that heat shock proteins and other proteins secreted from the endoplasmic reticulum may be recaptured by receptors known as erd-2 (KDEL) receptors and returned to the endoplasmic reticulum. This recapture process requires the presence of a specific retention sequence on the heat shock protein such XDEL. XDEL is the single letter amino-acid code for the amino acid sequence variable-Asp-Glu-Leu. Specific carboxy-terminal retention sequences are KDEL (Lys-Asp-Glu-Leu) and HDEL (His-Asp-Glu-Leu). By eliminating this retention sequence in heat shock proteins which bind to antigens or by otherwise interfering with the ability of the erd-2 receptor to recapture these heat shock proteins, the amount of antigen-associated heat shock protein secreted by a cell and therefore accessible to the immune system can be increased.

In accordance with either of these mechanisms, the stimulation of the immune response which is observed when an expressible polynucleotide encoding a heat shock protein is expressed in the cell flows from an increase in the amount of antigen-associated heat shock protein. Thus, in accordance with one embodiment of the invention there is provided a method for stimulating an immune response to an antigen present in a target group of mammalian cells, comprising administering to the target group of cells a composition effective to increase the amount of antigen-associated heat shock protein present in the cells. This can be accomplished in several ways.

First, the amount of antigen-associated heat shock protein can be increased by administering a polynucleotide encoding a heat shock protein which is expressed to produce recombinant heat shock protein that is processed and transported within the cell in the same manner as wild-type heat shock protein.

Second, the amount of antigen-associated heat shock protein can be increased by administering an expressible polynucleotide encoding a heat shock protein in a modified form adapted to control the trafficking of the expressed heat shock protein within the cells. This would include alterations of heat shock protein which either facilitate its secretion from the cell or its localization and/or retention on the cell. For example, secretion may be facilitated by mutating or eliminating portions of the heat shock protein that serve to retain the heat shock protein in the cell (for example by deleting sequences recognized by the erd-2 receptor such as KDEL or a functionally equivalent sequence or by adding an agent that interferes with binding of heat shock protein to erd-2), or by supplying mutated non-heat shock proteins (e.g. erd-2 mutants) that increase heat shock protein secretion. Alternatively localization and retention may be accomplished by increasing the number and/or strength of retention or retrieval signals (e.g. increasing erd-2 levels) or my by adding to a heat shock protein, a membrane anchor containing additional retention or retrieval sequence as well as transmembrane and cytoplasmic domains (e.g., KKXX at the C-terminal end, or XXRR at the N-terminal end or function equivalents thereof.)

Third, the amount of an antigen-associated heat shock protein can be increased by administering an expressible polynucleotide encoding a peptide or peptide which competitively inhibits the interaction of heat shock proteins with cellular elements to modify the trafficking of those heat shock proteins within the cell.

Preparation of Expressible Polynucleotides

The construction of expressible polynucleotides for use in the three embodiments of the invention share many common elements and use generally well known techniques. These techniques are set forth in numerous literature references known to persons skilled in the art and so will not be repeated exhaustively here.

Expressible polynucleotide encoding a heat shock protein which is expressed to produce recombinant heat shock protein that is processed and transported within the cell in the same manner as wild-type heat shock protein can be constructed by incorporating a cDNA encoding a wild-type heat shock protein or a modified heat shock protein that retains both its heat shock protein functionality and the XDEL retention sequence into a mammalian expression vector. Genes for various mammalian heat shock proteins have been cloned and sequenced, including, but not limited to, gp96, human: Genebank Accession No. X15187; Maki et al., *Proc. Nat'l Acad. Sci.* 87: 5658–5562 (1990), mouse: Genebank Accession No. M16370; Srivastava et al., *Proc. Nat'l Acad. Sci.* 84:3807–3811 (1987)); BiP, mouse: Genebank Accession No. U16277; Haas et al., Proc. Nat'l Acad. Sci. U.S.A. 85: 2250–2254 (1988), human: Genebank Accession No. M19645; Ting et al., DNA 7: 275–286 (1988); hsp70, mouse: Genebank Accession No. M35021; Hunt et al., *Gene* 87: 199–204 (1990), human: Genebank Accession No. M24743; Hunt et al., Proc. Nat'l Acad. Sci. U.S.A. 82: 6455–6489 (1995); and hsp40 human: Genebank Accession No. D49547; Ohtsuka K., *Biochem Biophys. Res. Commun.* 197: 235–240 (1993).

In general, any type of mammalian expression vector can be used, although those with the highest transfection and expression efficiencies are preferred to maximize the levels of expression. Specific types of vectors which can be employed include herpes simplex viral based vectors: pHSV1 (Geller et al. Proc. Natl. Acad. Sci 87:8950–8954 (1990)); recombinant retroviral vectors: MFG (Jaffee et al. Cancer Res. 53:2221–2226 (1993)); Moloney-based retroviral vectors: LN, LNSX, LNCX, LXSN (Miller and Rosman Biotechniques 7:980–989 (1989)); vaccinia viral vector: MVA (Sutter and Moss Proc. Natl. Acad. Sci. 89:10847–10851 (1992)); recombinant adenovirus vectors: pJM17 (Ali et al Gene Therapy 1:367–384 (1994)), (Berkner K. L. Biotechniques 6:616–624 1988); second generation adenovirus vector: DE1/DE4 adenoviral vectors (Wang and Finer Nature Medicine 2:714–716 (1996) ); and Adeno-associated viral vectors: AAV/Neo (Muro-Cacho et al. J. Immunotherapy 11:231–237 (1992)). Specific suitable expression systems for this purpose include pCDNA3 (In-Vitrogen), plasmid AH5 (which contains the SV40 origin and the adenovirus major late promoter), pRC/CMV (In-Vitrogen), pCMU II (Paabo et al., EMBO J. 5: 1921–1927 (1986)), pZip-Neo SV (Cepko et al., Cell 37: 1053–1062 (1984)) and pSRα (DNAX, Palo Alto, Calif.).

Expressible polynucleotides encoding any of the various modified forms heat shock proteins described above are constructed using similar techniques. For example, heat shock proteins can be produced which are modified to delete or block the carboxy-terminal XDEL sequence. Such a heat shock protein is adapted to permit the heat shock protein to be secreted from the endoplasmic reticulum and to interfere with the return of the protein to the endoplasmic reticulum that is mediated by the erd-2 receptors because the signal peptide recognized by the erd-2 receptors is missing. Proteins of this type are referred to in the specification and claims of this application as XDEL-negative heat shock proteins.

Expressible XDEL-negative polynucleotides can be constructed by deleting the nucleotides encoding the amino acid sequence XDEL at the carboxy-terminus of the heat shock protein. This can be accomplished by PCR amplification of the wild-type cDNA using a primer that hybridizes in the region immediately adjacent to the portion coding for the XDEL signal, combined with a restriction site to be used for cloning the product into a desired vector for expression of the modified heat shock protein in mammalian cells as described above.

As an alternative to the use of expressible polynucleotides encoding deletion mutants of heat shock proteins, the method of the invention may also employ expressible polynucleotides which encode heat shock proteins in which the carboxy-terminal retention sequence XDEL is masked by the addition of additional amino acids to the carboxy-terminal end. The masking amino acids can serve only the masking function, or can be derived from an infectious agent (for example E7/E6 from human papilloma virus) in which case the masking amino acids may also function as an antigen.

Addition of masking amino acids can be accomplished as described in Munro et al., Cell 48: 899–907 (1987) in which a mutant (SAGGL) having two amino acids added after the XDEL was prepared by cloning in appropriate restriction sites to permit substitution of a sequence including the additional bases, or by PCR amplification of the heat shock protein using a primer that hybridizes with the bases encoding the XDEL retention sequence and which has additional bases encoding the added nucleotides inserted between the XDEL-encoding bases and the stop codon. The number of additional amino acids does not matter, so long as the added amino acids do not alter the function of the heat shock protein. The nucleotides encoding the masked heat shock protein are then introduced into a mammalian expression vector as described above.

Another method which may be used to increase the amount of antigen-associated heat shock protein in the cells is to modify cytosolic heat shock proteins with an amino-terminal signal which causes the protein to be taken up into the endoplasmic reticulum where it can gain access to the secretory pathway. Amino-terminal signals which can accomplish this function are described in the art, including for example in von Heijne, G., J. Mol. Biol. 184: 99–105 (1985). These signals generally comprise a positively-charged amino acid or group of a few amino acids at the amino terminal end of the peptide, a hydrophobic core region and a third region of greater polarity than the hydrophobic region. Such additional signal sequences can be introduced using PCR with a modified primer that includes the bases for the desired amino-terminal amino acids. A representative cytosolic heat shock protein which might be modified in this manner is hsp 70.

The expressible polynucleotide used in the method of the present invention may also encode a peptide or protein that competitively inhibits the interaction of heat shock proteins with cellular elements to modify the trafficking of those heat shock proteins within the cell. In particular, the expressible polynucleotide may encode a peptide or protein that includes a carboxy-terminal XDEL retention sequence which will compete with heat shock proteins, including endogenous heat shock proteins, for binding to the erd-2 receptors. This competitive peptide may itself be a heat shock protein, for example BiP, that retains the XDEL retention sequence, or it may be some other peptide or protein with a carboxy-terminal XDEL sequence.

Administration of Expressible Polynucleotides

The resulting expressible polynucleotide is delivered into cells of the subject by ex vivo or in vivo methods, for example as part of a viral vector as described above, or as naked DNA. Suitable methods include injection directly into tissue and tumors, transfection using liposomes (Fraley et al, Nature 370: 111–117 (1980)), receptor-mediated endocytosis (Zatloukal, et al., Ann. N.Y. Acad. Sci. 660: 136–153 (1992)), particle bombardment-mediated gene transfer (Eisenbraun et al., DNA & Cell. Biol. 12: 791–797 (1993)) and transfection using peptide presenting bacteriophage. Barry et al. Nature Medicine 2: 299–305 (1996).

The expressible polynucleotide may be administered to a subject in need of treatment in order to obtain a therapeutic immune response. The term "therapeutic immune response", as used herein, refers to an increase in humoral and/or cellular immunity, as measured by standard techniques, which is directed toward an antigen associated with the subject's disease condition. Preferably, but not by way of limitation, the induced level of humoral immunity directed toward the antigen is at least four-fold, and preferably at least 16-fold greater than the levels of the humoral immunity directed toward the antigen prior to the administration of the expressible polynucleotide of this invention to the subject. The immune response may also be measured qualitatively, by means of a suitable in vitro assay or in viro, wherein an arrest in progression or a remission of neoplastic or infectious disease in the subject is considered to indicate the induction of a therapeutic immune response.

A further aspect of the invention is the administration of an expressible polynucleotide in combination with other forms of treatment including surgery, radiation therapy, and chemotherapy, to provide a vaccination against recurrence of cancer. By priming the immune system of subjects to recognize the cancer cells of their own cancers, the immune system will be more prepared to counter a subsequent regrowth, thus improving the prognosis for the subjects.

This same type of vaccination can be used to improve a subject's resistance to recurrent diseases, including many parasitic and viral diseases. Thus, the expressible polynucleotides of the invention may be administered to stimulate a prophylactic immune response. The term "prophylactic immune response", as used herein, refers to an increase in long term humoral and/or cellular immunity, as measured by standard techniques, which is directed toward an antigen associated with the subject's disease condition. In general, the prophylactic immune response is measured qualitatively, wherein a delay in the onset of recurring system is achieved.

The subject treated in the method of the invention may be a human or non-human subject.

In various embodiments of the invention, the polynucleotide may encode a heat shock protein derived from the same species or alternatively from a different species relative to the species of the subject.

The cells into which the expressible polynucleotide are introduced may be neoplastic cells or other cancer cells from the subject to be treated or vaccinated. In particular, the method of the invention is usefully applied to treat or vaccinate subjects suffering from cancer including solid tumors and neoplastic disease such as sarcoma, lymphoma, carcinoma, leukemia and melanoma. The method of the invention may also be utilized to stimulate an immune response to infectious diseases, including parasitic, fungal, yeast, bacterial, mycoplasmal and viral diseases, where a particular class of cells can be identified as harboring the infective entity. For example, but not by way of limitation, the cells treated may be infected with a human papilloma virus, a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae,* a bacterium of the genus Salmonella, Staphylococcus, Streptococcus, Enterococcus, Clostridium, Escherichia, Klebsiella, Vibrio, Mycobacterium, amoeba, a malarial parasite, Trypanosoma cruzi, etc. Thus, for example, in the case of human papilloma virus (HPV), the expressible polynucleotide could be introduced into epithelial cells infected with HPV from the subject to be treated.

The method of the invention can be practiced using various compositions. One such composition of matter is a recombinant vector comprising a promoter system effective to promote expression of the vector in mammalian cells; and a region encoding a XDEL-negative heat shock protein. The vector may be one in which the bases encoding a XDEL-retention sequence have been deleted from the region encoding the heat shock protein, or one in which additional bases have been added to the region encoding the heat shock protein to mask the XDEL-retention sequence in the expressed product. An exemplary vector would include gp96, preferably human gp96, as the heat shock protein.

A further composition of matter in accordance with the invention is a recombinant vector comprising a promoter system effective to promote expression of the vector in mammalian cells; and a region encoding a cytosolic heat shock protein such as hsp70 to which a signal comprising a positively-charged amino acid or group of a few amino acids at the amino terminal end of the peptide, a hydrophobic core region and a third region of greater polarity than the hydrophobic region is attached to promote uptake of the expressed cytosolic heat shock protein by the endoplasmic reticulum has been added.

The invention will now be further described by way of the following non-limiting examples.

EXAMPLE 1

Preparation of XDEL Deletion Mutants

The preparation of mammalian expression vectors encoding full-length and KDEL-deleted Drosophila BiP cDNAs (dBiP, also referred to a grp78) is described in Munro et al., *Cell* 48: 899–907 (1987). The expression vector encoding dBIP with a KDEL deletion (KDEL-deleted dBiP, SAGM2) has the KDEL retention sequence replaced with a c-myc sequence in a modified AHP2 plasmid. A further construct, WT dBiP (SAGMK1) has the c-myc sequence inserted between the KDEL retention sequence and the balance of the dBiP.

Wild type mouse BiP cDNA was cloned into plasmid pBSBiP. Haas, *Proc. Nat'l Acad. Sci. USA* 85: 2250–2254 (1988) In this plasmid, the BiP sequence is flanked by BamH I sites. The BamH I fragment was therefore recovered from pBSBiP and cloned into the BamH I site of mammalian expression vector pCDNA3 (In-Vitrogen). Mouse KDEL-deleted BiP was constructed using pCDNA3 by cloning the Bgl II-EcoR V PCR fragment (nucleotide 1360 to nucleotide 1981) of BiP using two oligonucleotide primers complementary to BiP. The nucleotides coding for the last four amino acids (KDEL) were omitted, and a stop codon and an EcoR V restriction site put in its place.

EXAMPLE 2

Preparation of Tumor Cells Expressing BiP

CMS-5 sarcoma cells, a methylocholanthrene-induced fibrosarcoma of BALD/c mouse origin, were adapted to culture and grown in DMEM medium (Gibco Life Technologies, Inc.) supplemented with 10% FCS. Sub-confluent monolayers ($2 \times 10^9$ cells) were transfected with 2 ug of mammalian expression vector containing BiP or KDEL-deleted BiP using lipofectamine (Gibco) according to the manufacturer's directions. Briefly, the expression vector and 6 ul of lipofectamine were diluted separately in 100 uL serum-free medium (OPTIMEM® I Reduced Serum Medium, Gibco-BRL). The two solutions were then mixed and incubated at room temperature for 45 minutes to allow formation of DNA-liposome complexes. 800 uL OPTI-MEMO® was added to the complexes, mixed, and overlaid onto rinsed cells. After a 6 hour incubation at 37° C., 1 mL growth medium containing 20% FCS was added. Fresh medium was added to the cells 24 hours post-transfection.

Stable clones were selected by adding 800 ug/mL geneticin (Gibco-BRL) to the cells 72 hours later. The selection medium was changed every 3 days. Colonies of stably transfected cells were seen after 10 to 14 days. Expression of BiP for each clone picked was assayed for by radiolabeling. Newly synthesized BiP was detectable by immunoprecipitation and gel electrophoresis.

Acutely (transiently) BiP expressing clones were trypsinized and used for animal injection 60 hours post-transfection.

EXAMPLE 3

Vaccination With BiP Expressing Tumor Cells

Figure 1A:
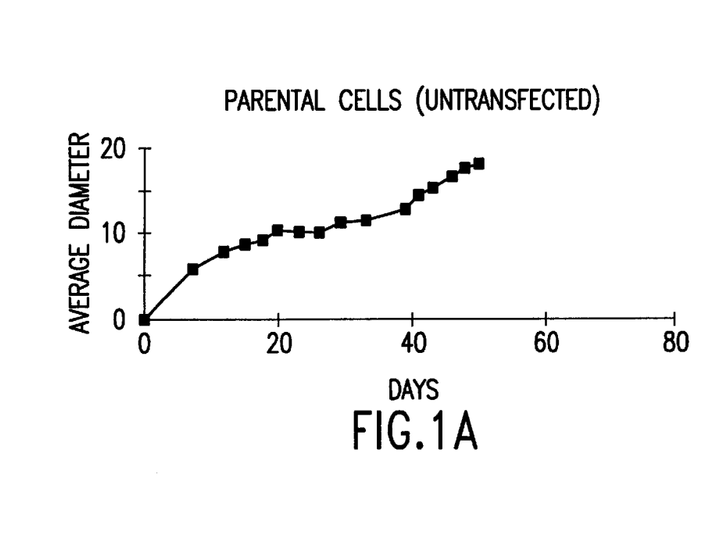
FIGS. 1A–H show tumor formation in mice injected with CMS-5 sarcoma cells and CMS-5 sarcoma cells acutely transfected with BiP-expressing vectors.
Figure 1B:
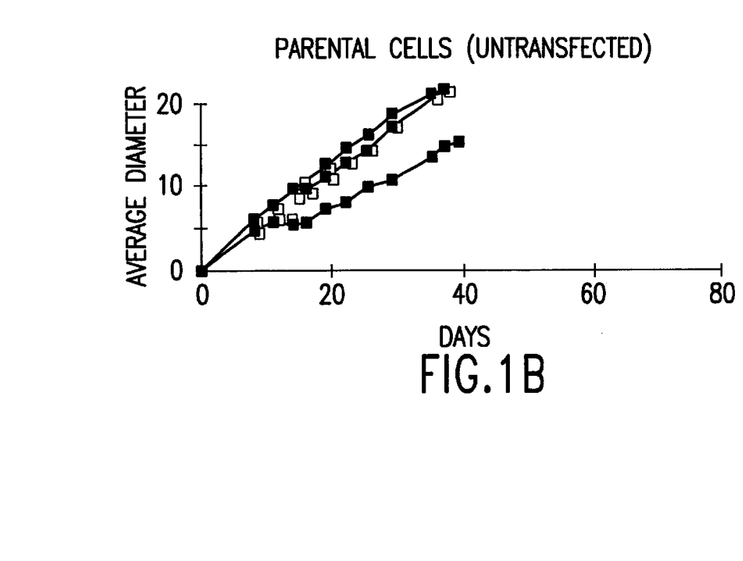
Figure 1C:
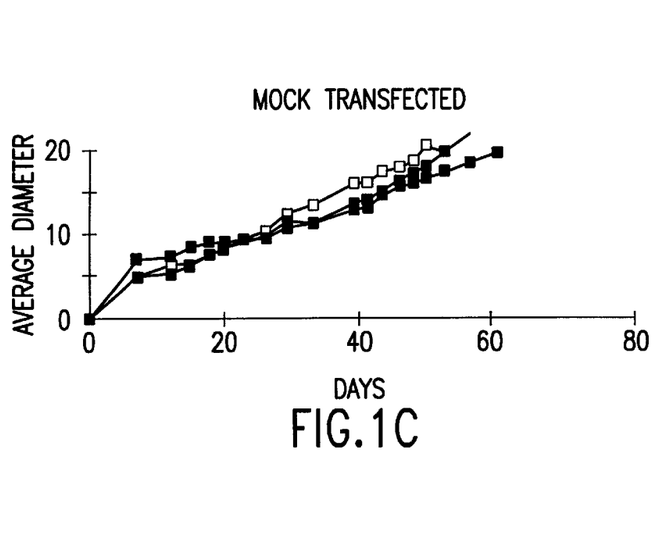
Figure 1D:
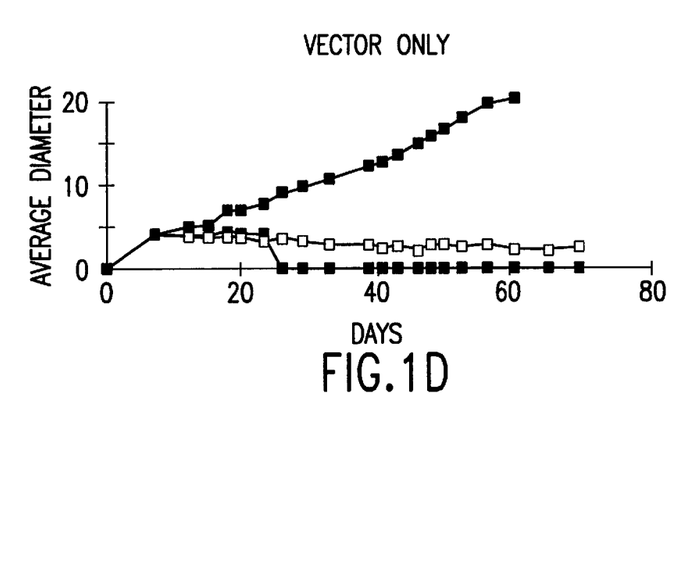
Figure 1E:
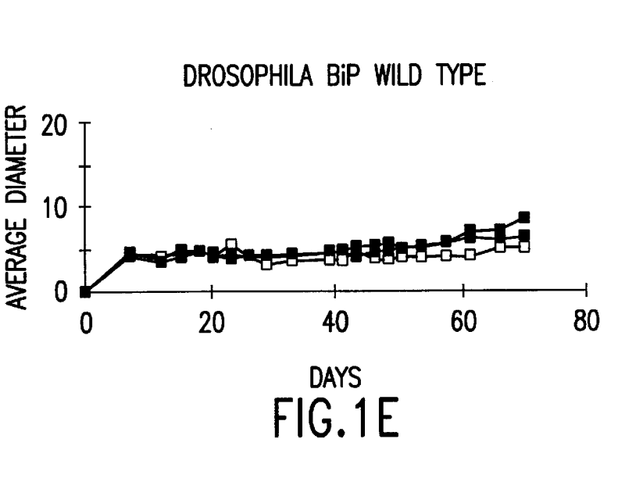
Figure 1F:
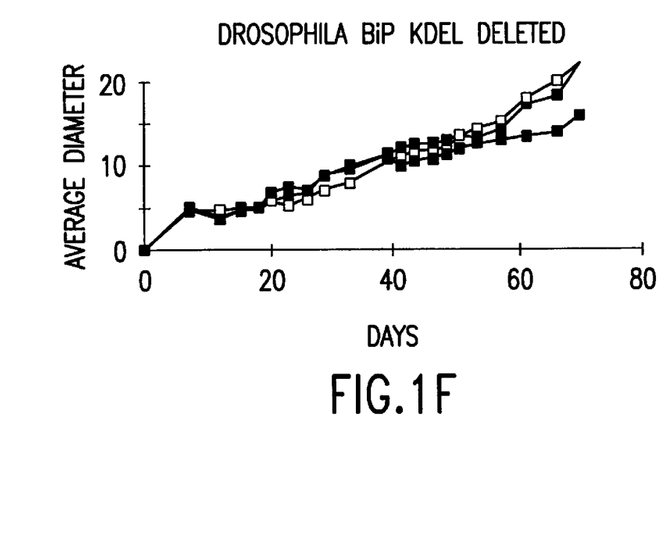
Figure 1G:
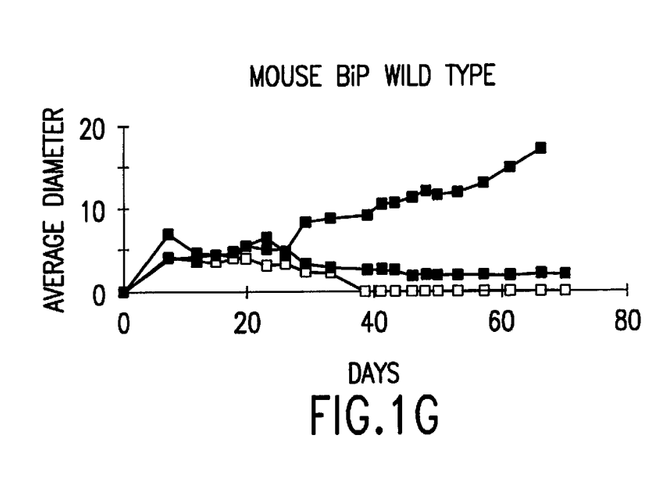
Figure 1H:
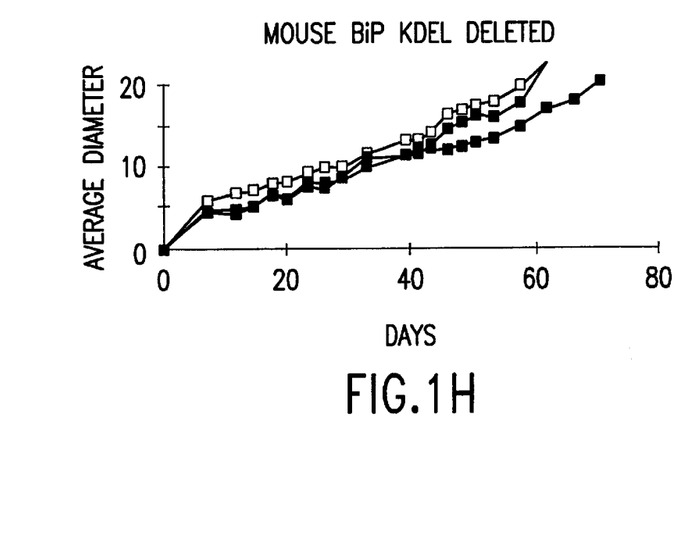

Freshly prepared acutely transfected CMS-5 sarcoma cells prepared in accordance with Example 2 were prepared for use in vaccination of mice by trypsinization and then washing three times in PBS. $2 \times 10^6$ cells were injected intradermally into the abdomen of CB6F-1/J [Balb/c× C57BL/6F1] mice (Jackson Laboratories) and monitored for tumor growth over a 90 day period. The results are summarized in Table 1 and shown graphically in Figs. 1A–H. As shown, injection with the parental CMS-5 sarcoma cells, with mock transfected cells, and with cells transfected with KDEL-deleted vectors led in all cases to the formation of tumors. Tumors also developed in one control mouse where the cells were transfected with the vector only (no BiP). On the other hand, only one of six mice transfected with the complete wild-type drosophila BiP (including the c-myc) or wild-type mouse BiP developed tumors.

TABLE 1

| Cell Line | Number of Tumor Free Mice per number of mice injected | Percent Tumor Free Survivals |
| --- | --- | --- |
| Parental CMS5 | 0/4 | 0% |
| Mock Transfected | 0/3 | 0% |
| Vector Only | 1/3 | 33% |
| Mouse BiP wild type | 2/3 | 66% |
| Mouse BiP KDEL deleted | 0/3 | 0% |
| Drosophila BiP wild type | 3/3 | 100% |
| Drosophila BiP KDEL deleted | 0/3 | 0% |

EXAMPLE 4

Figure 2A:
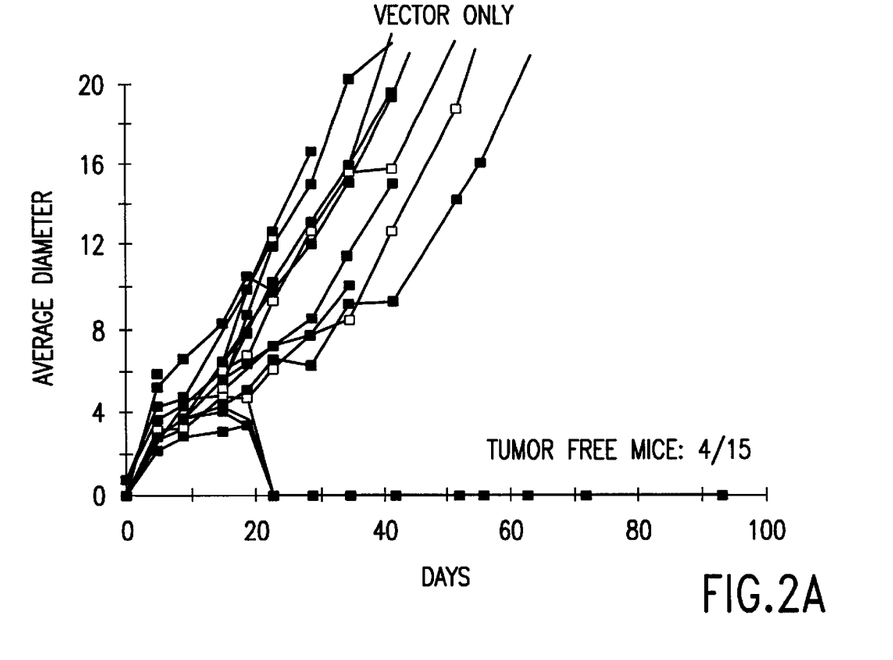
FIGS. 2A–F show tumor formation in mice injected with CMS-5 sarcoma cells and CMS-5 sarcoma cells stably transfected with BiP-expressing vectors.
Figure 2B:
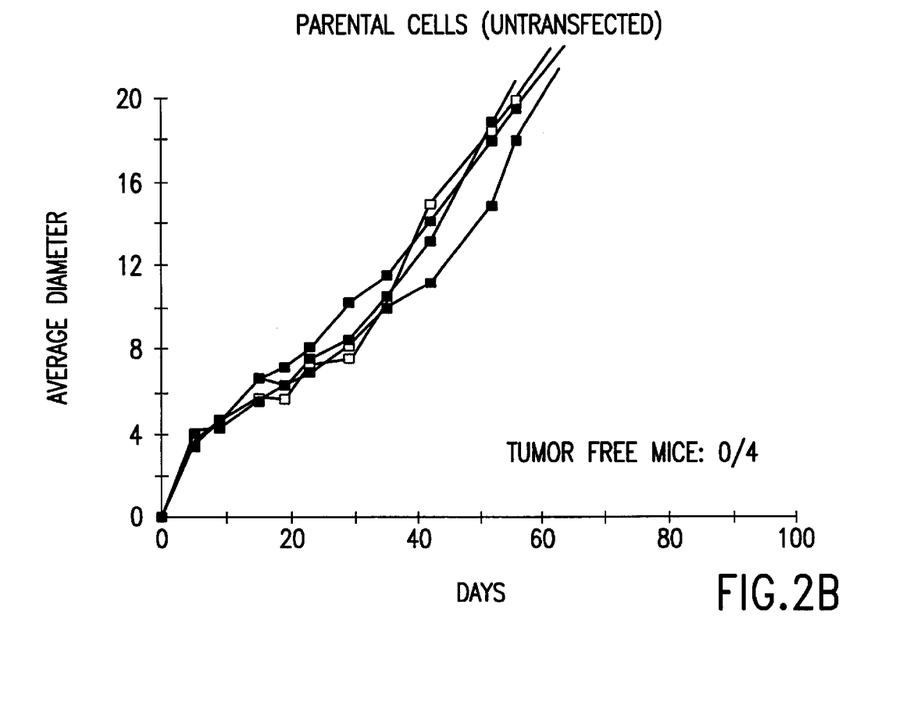
Figure 2C:
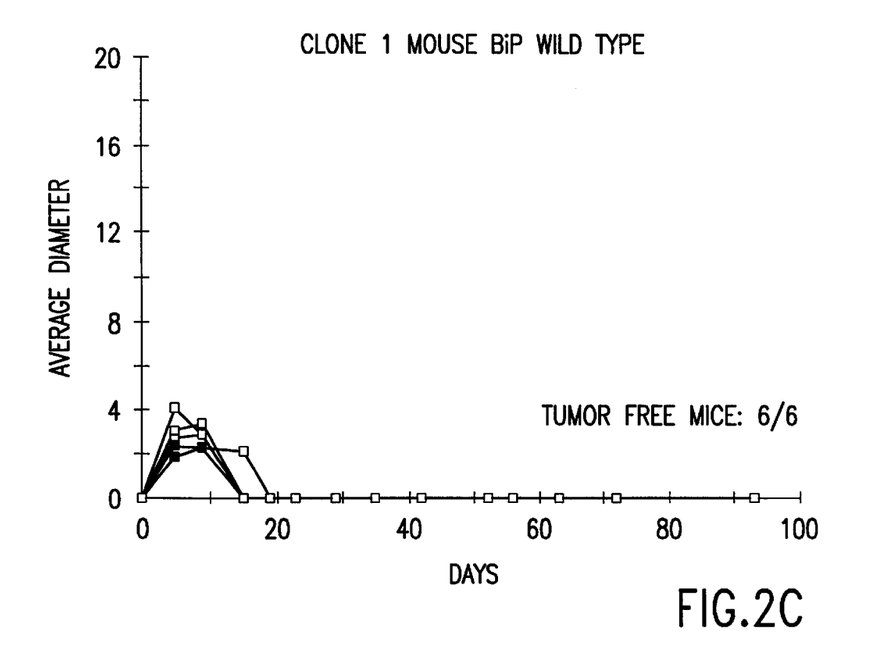
Figure 2D:
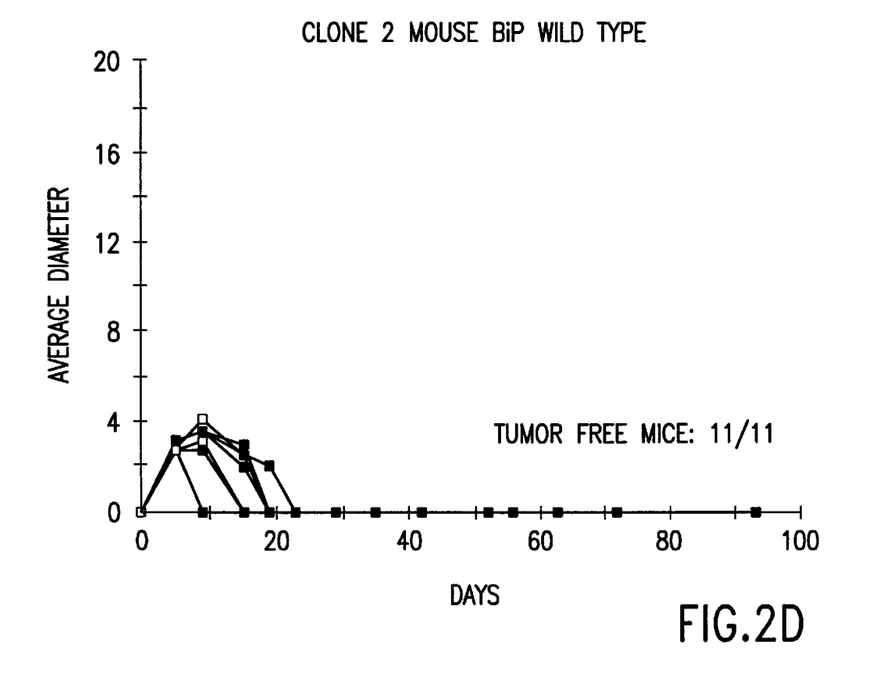
Figure 2E:
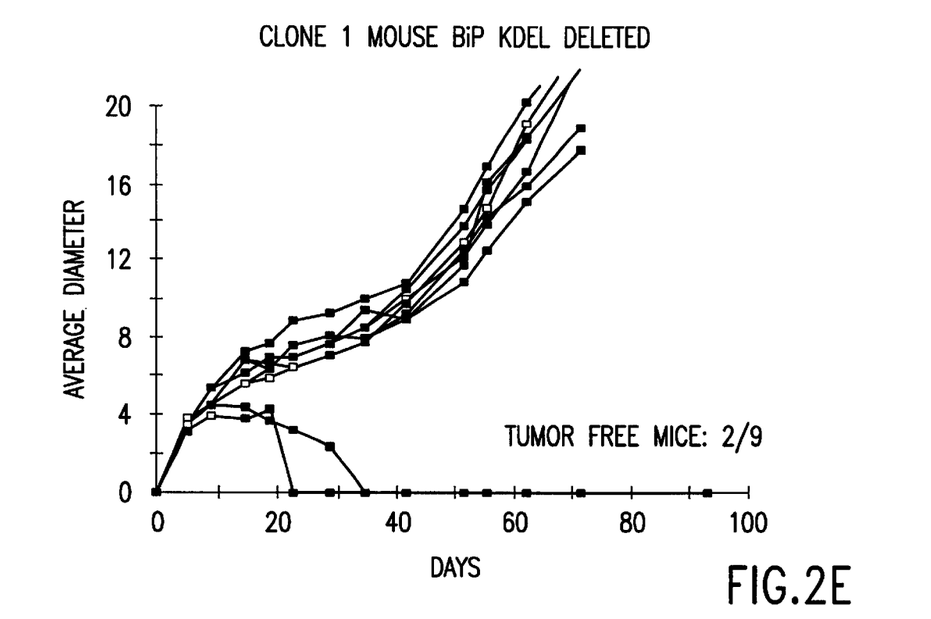
Figure 2F:
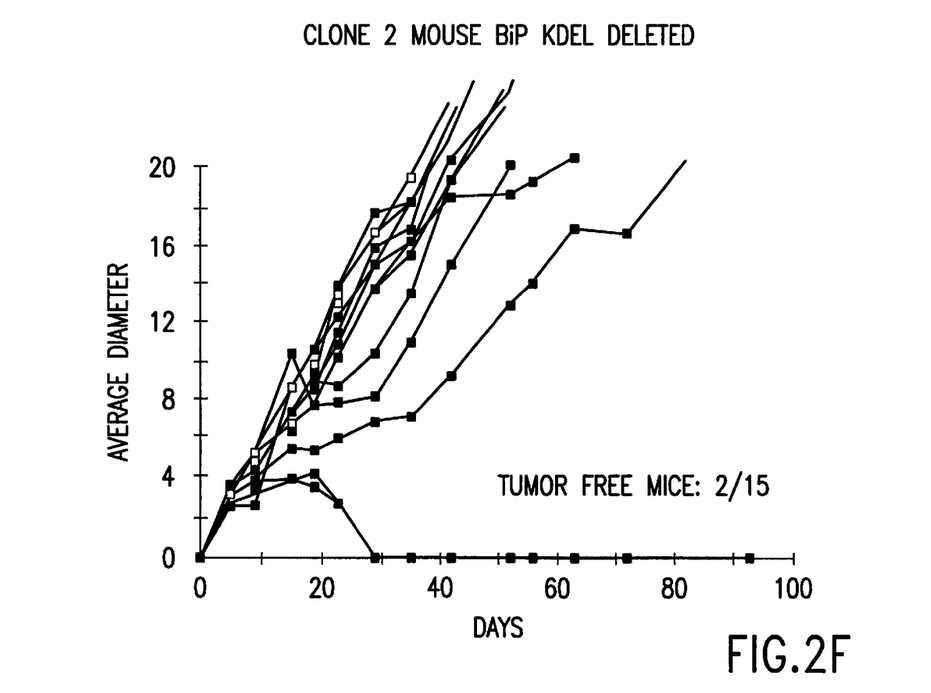

The experiment of Example 3 was repeated using larger groups of mice and using two different clones of stable mouse BiP-expressing transfected cells. As shown in Table 2 and FIGS. 2A–F, the results were essentially the same, with none of the mice injected with the vector expressing wild-type mouse BiP having any detected tumor formation.

TABLE 2

| Cell Lines | Number of Tumor Free mice per number of mice injected | Percent Tumor Free Survivals |
| --- | --- | --- |
| Parental CMS5 | 0/4 | 0% |
| Vector Only | 4/15 | 27% |
| Mouse BiP wild type: clone 1 | 6/6 | 100% |
| Mouse BiP wild type: clone 2 | 11/11 | 100% |
| Mouse BiP KDEL deleted: clone 1 | 1/9 | 11% |
| Mouse BiP KDEL deleted: clone 2 | 2/15 | 13% |

EXAMPLE 5

Tumor-free mice that had been injected with the wild-type BiP expression vector in the experiment of Example 4 were rechallenged after an interval of two months by injection of $2\times10^6$ or $10\times10^6$ CMS-5 sarcoma cells into the left flank of each mouse. Unimmunized CB6F-1/J mice of the same age group that had not been previously immunized were injected at the same time with $2\times10^6$ CMS-5 sarcoma cells as controls. As shown in Table 3, none of the previously immunized mice developed detectable tumors, while all three of the control mice developed tumors and died.

TABLE 3

| Rejected Tumor | Number of Tumor Free Mice/Number of Mice Injected | % Survivals |
| --- | --- | --- |
| Mouse BiP wild type: | 3/3 | 100% |
| clone 1 | 3/3 | 100% |
| Mouse BiP wild type: | 5/5 | 100% |
| clone 2 | 6/6 | 100% |
| Control | 0/3 | 0% |

EXAMPLE 6

Construction of Vector Expressing gp96

To create an expressible vector encoding gp96, the coding region of murine GP96 (mGP96) was digested with BamH I, blunted with Klenow and cloned into the Mammalian expression vector pRC/CMV (In-Vitrogen) which has been digested with Xba I and also blunted with Klenow. The resulting plasmid, p96/CMV was then used as template for generating a fragment spanning nucleotides 1653 to 2482 that lacks the nucleotides encoding the amino acids KDEL. The primers used for amplification of this fragment were 5' primer:

GCGGATCCTAGTTTAGACCAGTATGTC     [SEQ ID No. 1]

3' primer:

CCGAATTCGGGCCCCAAT
TTACTCTGTAGATTCCTTTTCTGTTT     [SEQ ID No. 2]

The restrictions sites for BamH I in the 5'-primer and EcoR I and Sal I in the 3'-primer are shown in bold italics. A stop codon (shown underlined) is provided four nucleotides from the Sal I restriction site in the 3'-primer. The BamH I/EcoR I PCR fragment was subcloned into pBlueScript II (Stratagene) to further amplify the amount of DNA. The amplified DNA was then digested with PflM I and Apa I, gel purified and subcloned into p96/CMV to give pMS215 which codes for KDEL-deleted gp96.

EXAMPLE 7

Vaccination With GP96 Expressing Vectors

Plasmids encoding the wt mGp96 (pMS216) and KDEL deleted mGp96 (215) are transfected into CMS-5 sarcoma cells as described in Example 2. 86 h post transfection, the acutely transfected CMS-5 sarcoma cells are trypsinized, washed in PBS and prepared for use in vaccination of mice as described in Example 3.

Various publications are cited herein, the contents of which are hereby incorporated by reference in their entireties.

What is claimed is:

1. A method for inhibiting the growth of a tumor in a mammalian subject, comprising (i) collecting from the subject a group of target cells harboring an antigen associated with the tumor; (ii) introducing ex vivo, a polynucleotide encoding a eukaryotic heat shock protein into the group of target cells, and then (iii) administering the group of target cells comprising the polynucleotide to the subject so as to inhibit the growth of the tumor, wherein the method does not include the step of isolating a eukaryotic heat shock protein originating from the tumor to inhibit the growth of the tumor.

2. The method according to claim 1, wherein the polynucleotide is introduced by transfection in a liposome.

3. A method for inhibiting the recurrence of a tumor from which a mammalian subject is suffering, comprising (i) collecting from the subject a group of target cells harboring an antigen associated with the tumor, (ii) introducing, ex vivo, into the group of target cells, a polynucleotide encoding a eukaryotic heat shock protein; and then (iii) administering the group of target cells comprising the polynucleotide to the subject so as to inhibit a growth of tumor cells that leads to the recurrence of the tumor, wherein the method does not include the step of isolating a eukaryotic heat shock protein originating from the tumor to inhibit the growth of tumor cells that leads to the recurrence of the tumor.

4. The method according to claim 3, wherein the polynucleotide is introduced by transfection in a liposome.

5. A method of stimulating an immune response against a diseased cell expressing an antigen in a mammalian subject, comprising (i) isolating the diseased cell; (ii) introducing, ex vivo, a polynucleotide encoding a eukaryotic heat shock protein in the diseased cell, (iii) administering the diseased cell comprising the polynucleotide to the subject, wherein the polynucleotide is expressed so as to stimulate the immune response in the subject against the diseased cell, and wherein the method does include the step of isolating a heat shock protein originating from the diseased cell to stimulate the immune response in the subject against the diseased cell.

6. The method according to claim 5, wherein the polynucleotide is introduced by transfection in a liposome.

* * * * *